United States Patent [19]

Stirling et al.

[11] 4,343,807
[45] Aug. 10, 1982

[54] DERIVATIVES OF CLAVULANIC ACID, A PROCESS FOR THEIR PREPARATION AND THEIR USE

[75] Inventors: Irene Stirling, Reigate; Brian P. Clarke, Kingswood, both of England

[73] Assignee: Beecham Group Limited, England

[21] Appl. No.: 190,463

[22] Filed: Sep. 24, 1980

[30] Foreign Application Priority Data

Sep. 27, 1979 [GB] United Kingdom ............... 7933447
Oct. 6, 1979 [GB] United Kingdom ............... 7934761

[51] Int. Cl.³ .................... C07D 498/04; A61K 31/42
[52] U.S. Cl. .................... 424/272; 260/245.3; 542/420
[58] Field of Search ............ 542/420; 424/272; 260/245.3

[56] References Cited

U.S. PATENT DOCUMENTS

| | | | |
|---|---|---|---|
| 3,926,955 | 12/1975 | Burton et al. | 424/271 |
| 4,229,443 | 10/1980 | Bendrup | 424/200 |
| 4,231,928 | 11/1980 | Naito et al. | 424/250 |
| 4,237,051 | 12/1980 | McCombie | 548/178 |
| 4,244,965 | 1/1981 | Howartt | 424/272 |
| 4,246,262 | 1/1981 | Vangedal | 424/244 |
| 4,252,772 | 2/1981 | Melillo | 424/244 |
| 4,278,686 | 7/1981 | Corbett | 424/274 |

FOREIGN PATENT DOCUMENTS 2747599 11/1978 Fed. Rep. of Germany .

OTHER PUBLICATIONS

Brook et al. *The Lancet,* Feb. 7, 1981, p. 332.
Stirling et al. *Chem Abs.* 92, 163955d (1979).

*Primary Examiner*—Mark L. Berch
*Attorney, Agent, or Firm*—Jacobs & Jacobs

[57] ABSTRACT

The compounds of the formula (II):

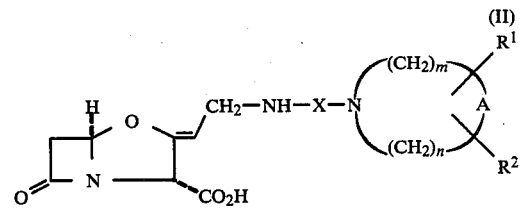

and pharmaceutically acceptable salts and esters thereof wherein X is a $C_{1-6}$ alkylene group; m is 1, 2 or 3; n is 1, 2 or 3; A is oxygen, sulphur, —$CH_2$— or —$NR^3$— wherein $R^3$ is hydrogen, $C_{1-6}$ alkyl, phenyl or phenyl ($C_{1-6}$)alkyl; $R^1$ is hydrogen, oxo, $C_{1-6}$ alkyl, $C_{1-6}$ alkoxy, hydroxy or phenyl; and $R^2$ is hydrogen, oxo, $C_{1-6}$ alkyl or phenyl: with the proviso that if m and n are both 1 then A is —$CH_2$— and $R^2$ is not oxo: have been found to be β-lactamase inhibitors and antibacterial agents. Their preparation and use are described.

114 Claims, No Drawings

DERIVATIVES OF CLAVULANIC ACID, A PROCESS FOR THEIR PREPARATION AND THEIR USE

This invention relates to a novel class of clavulanic acid derivatives and in particular to a class of heterocyclyl substituted alkylamine derivatives of clavulanic acid. These compounds have antibacterial and β-lactamase inhibitory qualities and therefore are of use in the treatment of bacterial infection either alone or in a synergistic composition with other antibacterial agents such as penicillins or cephalosporins.

Our earlier British patent application No. 16764/77 (corresponding to French Pat. No. 2387986, West German OLS No. 2817085, Japanese patent application No. 48292/78 and U.S. patent application Ser. No. 896441) filed Apr. 14, 1978, now abandoned, disclosed inter alia the compounds of the formula (I):

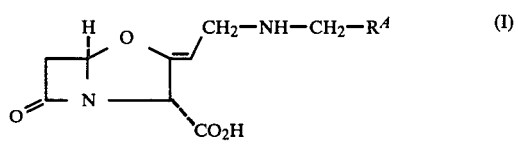

wherein $R^4$ is inter alia a hydrogen atom, an alkyl group of up to 5 carbon atoms, a cycloalkyl group of 5 to 6 carbon atoms or a hydroxyalkyl group of up to 5 carbon atoms.

The present invention provides the compounds of the formula (II):

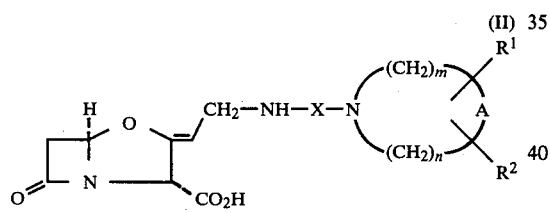

and pharmaceutically acceptable salts and esters thereof wherein X is a $C_{1-6}$ alkylene group; m is 1, 2 or 3; n is 1, 2 or 3; A is oxygen, sulphur, $-CH_2-$, a bond or $-NR^3-$ wherein $R^3$ is hydrogen, $C_{1-6}$ alkyl, phenyl or phenyl ($C_{1-6}$) alkyl; $R^1$ is hydrogen, oxo, $C_{1-6}$ alkyl, $C_{1-6}$ alkoxy, hydroxy or phenyl; and $R^2$ is hydrogen, oxo, $C_{1-6}$ alkyl or phenyl: with the proviso that if m and n are both 1 then A is $-CH_2-$ and $R^2$ is not oxo.

Suitably X is a $C_{1-6}$ alkylene group which may be straight-chained or branched. Thus suitable values for X include the methylene, ethylene, iso-propylene, trimethylene, tetramethylene, pentamethylene and hexamethylene groups. Preferably X is an ethylene or trimethylene group.

Suitably m is 1 or 2, more suitably m is 2. Suitably n is 1 or 2. A preferred combination is wherein m+n=3, a further preferred combination is wherein m+n=4.

A is suitably an oxygen or sulphur atom, of which oxygen is preferred. Suitably also A is a $-CH_2-$ or $-NR^3-$ group, of which $-CH_2-$ is preferred. Apt values of $-NR^3-$ include those wherein $R^3$ is hydrogen, phenyl, benzyl and $C_{1-6}$ alkyl for example methyl, ethyl and propyl.

$R^1$ is suitably a hydrogen atom or an oxo group or a $C_{1-6}$ alkyl group for example methyl, ethyl, propyl or butyl. Of these hydrogen, oxo, methyl and ethyl are favoured.

$R^2$ is suitably a hydrogen atom or an oxo group or a $C_{1-6}$ alkyl group for example methyl, ethyl, propyl or butyl. Of these hydrogen, oxo, methyl and ethyl are favoured.

Thus it will be evident that one preferred sub-group of compounds of this invention is that of the formula (III):

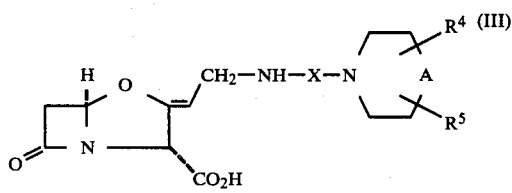

and pharmaceutically acceptable salts and esters thereof wherein X and A are as defined in relation to formula (II), and $R^4$ and $R^5$ are independently hydrogen or a $C_{1-6}$ alkyl group. Preferably in the compounds of the formula (III) A is an oxygen atom and $R^4$ and $R^5$ are independently hydrogen, methyl, ethyl or propyl. In another favoured aspect X is an ethylene or trimethylene group.

Another preferred sub-group of compounds of this invention is that of the formula (IV):

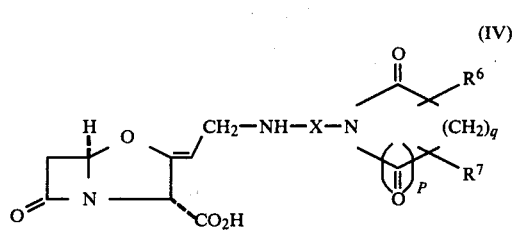

and pharmaceutically acceptable salts thereof wherein X is as defined in relation to formula (II), p is zero or 1, q is 2, 3 or 4; $R^6$ is a hydrogen atom, $C_{1-6}$ alkoxy, $C_{1-6}$ alkyl, hydroxy or phenyl; and $R^7$ is a hydrogen atom or a $C_{1-6}$ alkyl group.

Preferably p is zero. Suitably q is 2, 3 or 4, of these values q=3 is preferred.

Suitably $R^6$ is a hydrogen atom or a $C_{1-3}$ alkyl, $C_{1-3}$ alkoxy, phenyl or hydroxy group. More suitably $R^6$ is a hydrogen atom or a $C_{1-3}$ alkyl or phenyl group. Preferably $R^6$ is a hydrogen atom.

Suitably $R^7$ is a hydrogen atom or a $C_{1-3}$ alkyl or phenyl group, of these a preferred value for $R^7$ is hydrogen.

The compounds of this invention are preferably in the form of the free acid of formula (II), and as such normally exist in the form of a zwitterion, that is they may be represented as shown in formula (V):

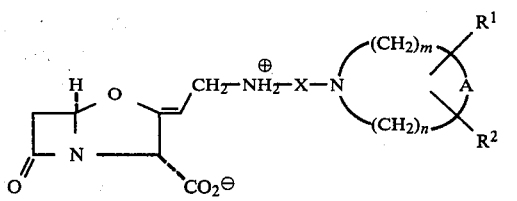

(V)

wherein X, m, n, A, $R^1$ and $R^2$ are as defined in relation to formula (II). These zwitterionic forms of the compounds are favoured in view of their crystalline form, stability and good solubility.

Thus preferred compounds of this invention include:
9-N-(2'-N-Morpholinoethyl)aminodeoxyclavulanic acid,
9-N-(3'-N-Morpholinopropyl)aminodeoxyclavulanic acid,
and 9-N-(3'-N-Pyrrolidinopropyl)aminodeoxyclavulanic acid.

Esters of the compounds of the formula (II) also form part of this invention, for example as the free base or as the acid addition salt since such compounds also can be used to enhance the effectiveness of penicillins and cephalosporins.

Suitable esters of the compounds of the formula (II) include those of the formula (VI):

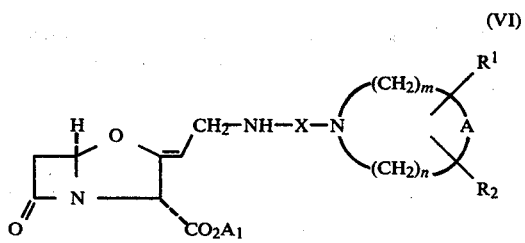

(VI)

wherein $A_1$ is a an alkyl group of 1-6 carbon atoms optionally substituted by an alkoxy or acyloxy group of 1-7 carbon atoms, or is a group of the sub-formula (a):

  (a)

wherein $A_2$ is an alkenyl or alkynyl group of up to 5 carbon atoms or is a phenyl group optionally substituted by a fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by a fluorine, chlorine, bromine, nitro or alkyl or alkoxyl of up to 4 carbon atoms.

Suitable values for $A_1$ include the methyl, ethyl, n-propyl, n-butyl, allyl, 2-methylallyl, $CH_2-C\equiv CH$, methoxymethyl, acetoxymethyl, propionoxymethyl, pivaloyloxymethyl, ethoxycarbonyloxymethyl, methoxycarbonyloxyethyl, ethoxycarbonyloxyethyl, phthalidyl, dimethoxyphthalidyl, benzyl, methoxybenzyl, ethoxybenzyl, nitrobenzyl and chlorobenzyl groups.

Certain favoured values $A_1$ include the methyl, ethyl, propyl, methoxy, acetoxymethyl, acetoxyethyl, phthalidyl, ethoxycarbonyloxymethyl and α-ethoxycarbonyloxyethyl.

Certain favoured groups $A_2$ include the phenyl and 4-methoxyphenyl groups. A particularly favoured moiety $A_3$ is the hydrogen atom.

Certain other favoured values for $A_1$ include those of the sub-formulae (b), (c) and (d):

  (b)

  (c)

  (d)

wherein $A_4$ is a hydrogen atom or a methyl group and $A_5$ is an alkyl group of up to 4 carbon atoms or a phenyl or benzyl group either of which may be substituted by one or two alkyl or alkoxyl groups of up to 3 carbon atoms or by a fluorine, chlorine or bromine atom or a nitro group; or $A_4$ is joined to $A_5$ to form the residue of an unsubstituted saturated 5- or 6-membered heteroalicyclic ring or an orthophenylene group which may be substituted by one or two alkyl or alkoxyl groups of up to 3 carbon atoms or by a fluorine, chlorine or bromine atom or nitro group.

An apt acyclic value for the sub-group of the formula (b) is $-CH_2-OA_5$.

An apt acyclic value for the sub-group of the formula (c) is $-CH_2-CO-A_5$.

An apt acyclic value for the sub-group of the formula (d) is $-CH_2-CO_2A_5$.

A further apt acyclic value for the sub-group of the formula (d) is $-CH(CH_3)-CO_2A_5$.

Favoured values for $A_5$ in the preceding acyclic moieties include the methyl, ethyl, propyl, butyl, phenyl and benzyl groups.

Apt cyclic values for the sub-group of the formula (c) include the tetrahydropyranyl and tetrahydrofuranyl groups.

Esters of the compounds of the formula (II) such as those of the compounds of the formula (VI) may be presented in the form of their acid addition salts if desired. The acid used to form the salt will most suitably be pharmaceutically acceptable, but non-pharmaceutically acceptable acid addition salts are also envisaged, for example as intermediates in the preparation of the pharmaceutically acceptable salts by ion exchange. Suitable pharmaceutically acceptable acid addition salts include those of inorganic and organic acids, such as hydrochloric, phosphoric, sulphuric, methanesulphonic, toluenesulphonic, citric, malic, acetic, lactic, tartaric, propionic and succinic acid.

Most suitably the acid addition salt is provided as a solid and preferably as a crystalline solid.

Compounds of this invention when in crystalline form may be solvated, for example hydrated.

The present invention provides a pharmaceutical composition which comprises a compound of this invention and a pharmaceutically acceptable carrier.

The compositions of the invention include those in a form adapted for oral, topical or parenteral use and may be used for the treatment of the infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

An alternative approach to administering the compounds of this invention and especially those zwitterionic compounds of the formula (II) is to utilise an injectable suspension. Such suspensions may be made up in sterile water, sterile saline or the like and may also contain suspending agents such as polyvinylpyrrolidone, lecithin or the like (for example in the manner described for amoxycillin trihydrate in Belgian Pat. No. 839,109). Alternatively such compositions may be prepared in an acceptable oil suspending agent such as arachis oil or its equivalent. The use of suspensions can give rise to advantageously prolonged blood levels of the medicament. Belgian Pat. No. 839,109 may be consulted for suitable methods and materials for producing injectable aqueous suspensions. For use in such suspensions the zwitterionic compound of this invention should be in the form of fine particles as described in said Belgian Patent.

Unit dose compositions comprising a compound of this invention adapted for oral administration form a further suitable composition aspect of this invention.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin since the resulting composition shows enhanced effectiveness (synergy).

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, and other known penicillins including pro-drugs therefore such as their in vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde or ketone adducts of penicillins containing a 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole, nafate, cephapirin, cephradine, 4-hydroxycephalexin, cefaparole, cephaloglycin, and other known cephalosporins or pro-drugs thereof.

Such compounds are frequently used in the form of a salt or hydrate of the like.

Naturally if the penicillin or cephalosporin present in the composition is not suitable for oral administration then the composition will be adapted for parenteral administration.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin which may be in the form of a pharmaceutically acceptable salt for example the sodium salt.

When present together with a cephalosporin or penicillin, the ratio of a compound of the invention to the penicillin or cephalosporin agent may vary over a wide range of ratios, such as from 10:1 to 1:10 for example about 3:1, 2:1, 1:1, 1:2, 1:3, 1:4, 1:5 or 1:6, (wt/wt, based on pure free antibiotic equivalent). Orally adminstrable compositions containing a compound of the invention will normally contain relatively more synergist than corresponding injectable compositions.

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day of treatment but more usually between 100 and 750 mg of the compounds of the invention will be administered per day, for example at 1–6 doses, more usually as 2, 3 or 4 doses.

The penicillin or cephalosporin in the synergistic composition of this invention will normally be present at approximately the amount at which it is conveniently used which will usually be expected to be from about 62.5 to 1000 mg per dose, more usually about 125, 250 or 500 mg per dose.

One particularly favoured composition of this invention will contain from 150 to 1000 mg of amoxycillin as the trihydrate or sodium salt and from 25 to 500 mg of a compound of this invention.

Most suitably this form of composition will contain a compound of the formula (II) when in crystalline zwitterionic form.

A further particularly favoured composition of this invention will contain from 150 to 1000 mg of ampicillin or a pro-drug therefore and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitably this form of the composition will contain a compound of the formula (II) when in crystalline zwitterionic form.

Most suitably the preceding composition will contain from 200 to 700 mg of the penicillin component. Most suitably the preceding composition will comprise from 50 to 250 mg of a compound of the formula (II) preferably in crystalline zwitterionic form.

Such compositions may be adapted for oral or parenteral use except when containing an in vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefore and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formula (II) preferably in crystalline zwitterionic form. Such compositions containing di-salts of carbenicillin and ticarcillin will be adapted for parenteral administration.

The present invention also provides a method of treating bacterial infections in humans or domestic mammals which comprises the administration of a composition of this invention.

Commonly the infection treated will be due to a strain of *Staphylococcus aureus, Klebsiella aerogenes, Escherichia coli*, or *Proteus sp*. The organisms believed to be most readily treated by an antibacterially effective amount of a compound of this invention is *Staphylococcus aureus*. The other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

The present invention also provides a process for the preparation of a compound of the formula (II) or a pharmaceutically acceptable salt or ester thereof which process comprises removing a group $R^a$ from a compound of the formula (VII).

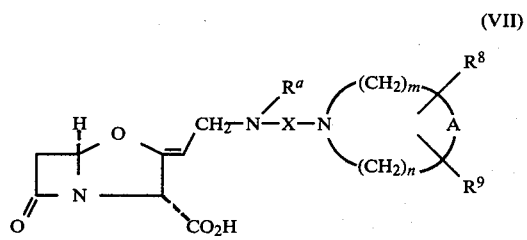
(VII)

or salt or ester thereof wherein X, m, n and A are as defined in relation to formula (II), $R^8$ and $R^9$ are groups $R^1$ and $R^2$ respectively or are groups convertible by chemical or biological means to groups $R^1$ and $R^2$ respectively wherein $R^1$ and $R^2$ are as hereinbefore defined and $R^a$ is a removable protecting group, and optionally thereafter carrying out one or more of the following steps:

(i) coverting an ester if present to the free acid or a salt or another ester,
(ii) converting the free acid or salt to an ester,
(iii) forming an acid addition salt of any such ester.

Suitably the group $R^a$ is one which may be removed by hydrogenation, for example $R^a$ may be a group of the subformula (e):

wherein $R^{10}$ is a hydrogen atom or $C_{1-6}$ alkyl group and $R^{11}$ is a hydrogen atom, a $C_{1-6}$ alkyl group, or a phenyl group optionally substituted by a $C_{1-6}$ alkoxy group; or $R^{10}$ and $R^{11}$ together with the carbon atoms to which they are joined represent a phenyl group. Suitably also $R^a$ may be a benzyloxycarbonyl group or substituted benzyloxycarbonyl group, that is a group of the sub-formula (f):

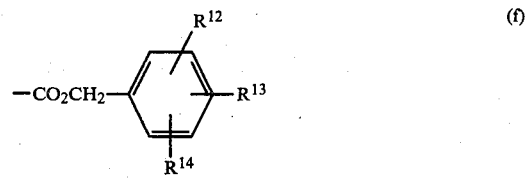

wherein $R^{12}$ is a hydrogen, fluorine, chlorine or bromine atom or an alkyl group of 1-3 carbon atoms, an alkoxyl group of 1-3 carbon atoms, an acyloxyl group of 1-3 carbon atoms, a hydroxyl group, an alkoxycarbonyl group containing 1-3 carbon atoms in the alkoxy part, or a group $—N(R^{15})CO.R^{16}, —N(R^{15})SO_2R^{16}$ or $—CO—NR^{15}R^{16}$ where $R^{15}$ is a hydrogen atom or an alkyl group of 1-3 carbon atoms or a phenyl or benzyl group and $R^{16}$ is an alkyl group of 1-3 carbon atoms or a phenyl or benzyl group; $R^{13}$ is a hydrogen, fluorine or chlorine atom or an alkyl group of 1-3 carbon atoms, an alkoxyl group of 1-3 carbon atoms or an acyloxyl group of 1-3 carbon atoms; and $R^{14}$ is a hydrogen fluorine or chlorine atom or an alkyl group of 1-3 carbon atoms or an alkoxyl group of 1-3 carbon atoms.

Particularly suitable groups $R^a$ include the following:
$CH_2CH=CHCH_3$,  $CH_2CH=CHC_6H_5$,
$CH_2C(CH_3)=CH_2$,  $CH_2C(C_2H_5)=CH_2$,
$CH_2C(nC_3H_7)=CH_2$,  $CH_2C(CH_3)=CHCH_3$,
$CH_2C(CH_3)=C(CH_3)_2$,  $CH_2C(CH_3)=CHC_2H_5$,
$CH_2C(CH_3)=CHC_6H_5$ and $CH_2C_6H_5$.

Favoured groups $R^a$ are $CH_2CH=CHCH_3$, $CH_2CH=CHC_6H_5$, $CH_2C(CH_3)=CH_2$, $CH_2C(CH_3)CH=C_6H_5$ and $CH_2C_6H_5$.

A preferred group $R^a$ is $CH_2C_6H_5$.

The hydrogenation is normally carried out in the presence of a transition metal catalyst.

The catalyst we have preferred to use is palladium, for example in the form of palladium on carbon (charcoal), palladium on barium sulphate, palladium on calcium carbonate, palladium black or the like.

A favoured catalyst is palladium on carbon (sometimes referred to as palladium on charcoal); for example 5%, 10%, 20% or 30% palladium on carbon.

A low, medium or high pressure of hydrogen may be used in this reaction, for example from 1 to 6 atmospheres.

The reaction is normally carried out at a nonextreme temperature, for example from 0° C. to 30° C. and more usually from 12° C. to 25° C. It is generally convenient to carry out the reaction at ambient temperature.

Suitable solvents for carrying out the hydrogenation include ethanol, n-propanol, isopropanol, tetrahydrofuran, dioxan, ethyl acetate or mixtures of such solvents or such solvents in the presence of water. A favoured solvent is ethanol.

We have preferred to carry out the hydrogenation reaction on a hydrogenolysable ester of a compound of the formula (VII) wherein R is a $CH_2C_6H_5$ group so that a compound of the formula (II) per se is formed by the hydrogenation. Such hydrogenation reactions proceed at least in part via the formation of a compound of the formula (VII). Favoured hydrogenolysable esters include benzyl and substituted benzyl esters such as methoxybenzyl, nitrobenzyl (for example the p-nitrobenzyl ester), chlorobenzyl and bromobenzyl esters. A particularly suitable hydrogenolysable ester is the p-methoxybenzyl ester. Further favoured hydrogenolysable ester groups include those groups $CH_2CR^{10}=CHR^{11}$ that have been specified hereinbefore as being favoured for removal from a nitrogen atom by hydrogenolysis.

If the hydrogenation is performed on a non-hydrolysable ester of the compound of the formula (VII) then naturally an ester of the compound of the formula (II) results.

The product may generally be isolated from the reaction mixture by filtering off the solids (the catalyst which should be well washed to remove the product) and then evaporating the solvent, preferably under low pressure, to yield the initial product. Further purification may be effected by such conventional methods as chromatography over cellulose or other mild stationary phase eluting with a $C_{1-4}$ alkanol optionally in the presence of ethyl acetate and water. A preferred purification method utilises a combination of ethyl acetate, isopropanol and water as the eluent over silica. A further preferred purification method utilises a combination of n-butanol, isopropanol and water as the eluent over cellulose. Evaporation of the combined active fraction (identified by aqueous potassium permanganate spray on tlc) then yields the desired compound in pure form. The desired product is normally obtained in crystalline form (unless it is an unsalted ester). Trituration under ethanol, isopropanol or the like $C_{1-4}$ alkanol or other conventional solvent such as a ketone, ether or ester solvent or other conventional solvent (for example of up to 6 carbon atoms and more suitably of up to 4 carbon atoms) may also be used to aid crystallisation. Recrystallisation from ethanol or the like may also be employed. The solvent used in such processes may advantageously be moist.

Certain unsalted esters of the compounds of the formula (II) are low melting so that it is often more convenient for handling to convert them into solid acid addition salts, for example by reaction with one equivalent of an acid. Alternatively the non-hydrogenolysable esters of the compound of the formula (VII) may be hydrogenated in the presence of one equivalent of an acid, that is they may be hydrogenated in the form of their acid addition salt.

An alternative method of hydrogenation suitable for use in this procedure is catalytic transfer hydrogenation using a transition metal catalyst. The transition metal catalyst employed is preferably palladium, for example palladium on carbon, palladium on barium sulphate or palladium black. It is preferred to use palladium on carbon for example 10% palladium on charcoal. Suitable solvents include those in which the ester is soluble for example ethanol, dimethylformamide, dimethylacetamide and mixtures thereof. In catalytic transfer hydrogenation a hydrogen donor is used (not hydrogen gas). Suitable hydrogen donors include cyclohexene and 1,4-cyclohexadiene. The reaction is conveniently performed at an elevated temperature suitably between ambient temperature and 100° C., more suitably between 30° C. and 80° C. It is sometimes suitable to perform the reaction at reflux temperature.

In an alternative aspect of this invention there is provided a process for the preparation of a compound of the formula (II) or a pharmaceutically acceptable salt or ester thereof which process comprises reacting a compound of the formula (VIII) or a salt or ester thereof:

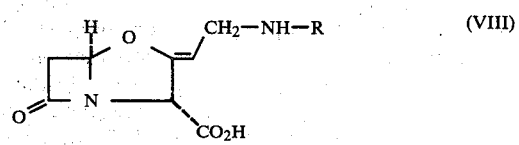

(VIII)

wherein R is a hydrogen atom or a group $R^a$ as hereinbefore defined; with a compound of the formula (IX):

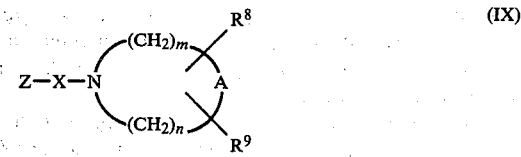

(IX)

wherein X, m, n, A, $R^8$ and $R^9$ are as hereinbefore defined and Z is a readily displaceable group, removing any group R that is not hydrogen, and optionally thereafter:

(i) converting an ester if present to the free acid or a salt or another ester,
(ii) converting the free acid or salt to an ester,
(iii) forming an acid addition salt of any such ester.

Preferably R is hydrogen, but it may conveniently be a silyl group such as trimethylsilyl or any of the groups $R^a$ as described above with respect to formula (VII).

Suitable groups Z include halides, for example bromide and iodide, and sulphonate esters, for example alkayl sulphonates and arylsulphonates, such as methanesulphonate; benzenesulphonate, p-toluenesulphonate and p-bromobenzenesulphonate.

Preferably Z is iodide.

The reaction of the compound of the formula (VIII) with the compound of the formula (IX) is conveniently carried out in an inert organic solvent such as dimethylformamide, acetonitrile or dichloromethane, preferably in the presence of a strong non-nucleophilic organic base such as diazabicyclononene or diazabicycloundecane at a non-extreme temperature for example $-10°$ C. to $+50°$ C., more usually $-5°$ C. to $+20°$ C. and most conveniently in the range $-5°$ C. to $+10°$ C.

The present invention also provides a process for the preparation of an ester of a compound of the formula (II) which process comprises the reaction of the compound of the formula (II) with an esterifying agent.

The zwitterionic compound of the formula (II) may be dissolved or suspended in a solvent such as dimethylformamide, hexamethylphosphoramide, dichloromethane, ethyl acetate or other non-esterifiable solvents and therein esterified. Suitable temperatures for such a reaction range from about 0° to about 25°. Suitable esterifying reagents include reactive halides and their equivalents, alkyl oxonium salts and the like.

When a reagent such as a reactive iodide, chloride, bromide, tosylate, mesylate or the equivalent is used, the resulting salt is generally suitable for use in a composition of this invention. Alternatively, the salt may be converted to a free base or alternative salt. When an alkyl oxonium salt is used, it is preferred to convert the resulting tetrafluoroborate to the free base or alternative salt. The various aforementioned salts may be converted to the free base by neutralisation, for example by contacting a solution of the salt in water with an organic phase, neutralising the salt by adding a base and extracting the liberated amine into the organic phase. This amine may thereafter be re-salted by reacting with an appropriate acid, for example in a dry organic solvent. It is generally preferred to use not more than one equivalent of acid for this process. Alternatively the originally formed salt may be converted into the alternative salt using an ion exchange material, for example, by passing an aqueous solution of one salt through a bed of an anion exchange resin in the form of the desired salt such as the chloride form.

The salts may normally be obtained in solid form by dissolving in a fairly polar organic solvent (such as ethanol, tetrahydrofuran or the like) and then precipitating using a non-polar solvent such as diethyl ether, cyclohexane or the like.

The salts of the esters of the compounds of the formula (II) may normally be obtained in crystalline form by conventional methods such as trituration under (or crystallisation or recrystallisation form) a suitable organic solvent such as ether, acetone, acetonitrile, tetrahydrofuran or the like.

The present invention also provides a process for the preparation of an ester of the compound of the formula (II) which process comprises the reaction of the compound of the formula (II) with an alcohol in the presence of a condensation promoting agent.

Suitable condensation promoting agents for use in this process include carbodiimides such as dicyclohexylcarbodiimide and the chemical equivalents thereof.

The acid addition salt may be formed in situ or may be preformed. The acid employed will normally be a strong acid such as a methane sulphonic acid, p-toluene sulphonic acid or the like or trifluoroacetic acid or the like.

The reaction is normally carried out in an inert organic solvent. When the ester being formed is that of a liquid alcohol it is convenient to use that alcohol as the solvent or as part of the solvent system. The esterification is generally performed at a non-extreme temperature such as 0°-35°, for example from about 10°-25° C. Conveniently the reaction mixture may be performed at ambient temperature.

The compounds of the formula (VII) may be prepared by the methods of U.K. Pat. No. 1,566,706 and aforementioned British Patent Application 16764/77. For example the compounds of the formula (VII) may be prepared by the reaction of a compound of the formula (X) or salt or ester thereof, or the reaction of an ester of the compound of the formula (XI):

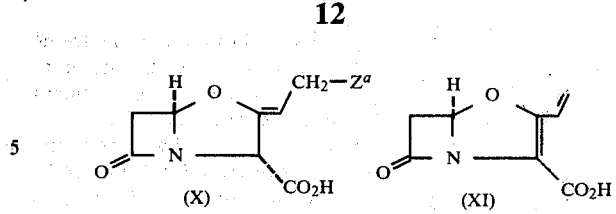

wherein $Z^a$ is a displaceable group; with an amine of the formula (XII):

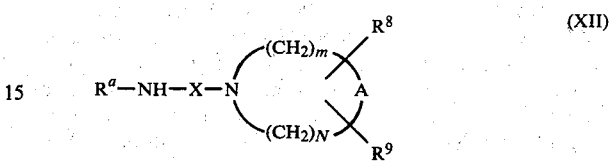

wherein $R^a$ m, n, $R^8$, $R^9$ and X are as hereinbefore defined.

The compounds of the formula (VIII) may be prepared by the methods of French Patent Application Publication No. 2353556 for the case wherein R is a hydrogen atom, or by the reaction of a compound of the formula(VIII) or salt or ester thereof wherein R is hydrogen with a compound of the formula $R^a$—Z wherein $R^a$ and Z are as hereinbefore defined. Alternatively certain compounds of the formula (VIII) may be prepared by the methods of French Patent Application Publication No. 2368490 and the aforementioned British Patent Application No. 16764/77.

The following Examples illustrate the invention.

DESCRIPTION 1

Benzyl 9-N-(2'-N-morpholinoethyl)-N-(2''-methyl-3''-phenylallylallyl) aminodeoxyclavulanate

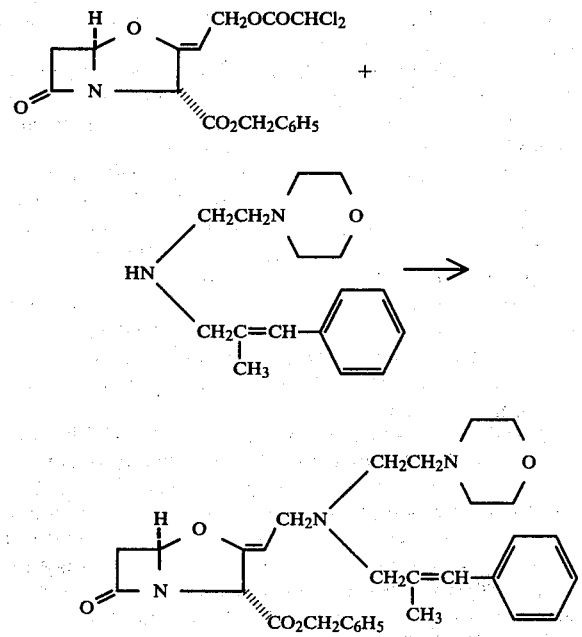

Benzyl dichloroacetylclavulanate (8.1 g; 20.2 mM) in dry dimethylformamide at −5° was treated with 1.9 equivalents of N(2-N-morpholinoethyl)-N-(2'-methyl-3'-phenylallyl)amine, dropwise with stirring. Stirring was continued for 1½ hours, after which the mixture was poured into ethyl acetate (300 cm³), washed with water (6×100 cm³), saturated brine (6×100 cm³), dried (anhydrous magnesium sulphate) and evaporated to an oil. This oil was chromatographed on silica eluting with methyl acetate. Fractions were collected containing the title compound Rf (SiO₂/ethylacetate)=0.44 (detection by aqueous potassium permanganate spray). The combined fractions were evaporated to afford the title compound as an oil (2.2 g) (20.5%), ν(film) 1805, 1750, 1697, 1450, 1305, 1175, 1115, 1010, 745, 700 cm⁻¹; δ(CDCl₃) 1.85

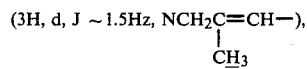
(3H, d, J ~1.5Hz, NCH₂C=CH—),
         |
        CH₃

2.28–270 (8H, m, NCH₂CH₂N and N(CH₂CH₂)₂O), 2.95 (1H, d, J 17 Hz, 6βCH), 3.01 (2H, s, NCH₂C(CH₃)=CH—), 3.23 (2H, d, J 7 Hz, 9CH₂), 3.42 (1H, dd, J 17 and 3 Hz, 6αCH), 3.46–3.80 (4H, m, (N(CH₂CH₂)₂O), 4.75 (1H, t, J 7 Hz, 8CH), 5.08 (1H, s, 3CH), 5.19 (2H, s, OCH₂C₆H₅), 5.63 (1H, d, J 3 Hz, 5αCH), 6.37 (1H, broad s, —C(CH₃)=CH—), 7.25 and 7.33 (10H, 2×s, 2×C₆H₅).

DESCRIPTION 2

Benzyl 9-N(2'-N-morpholinoethyl)benzylaminodeoxyclavulanate

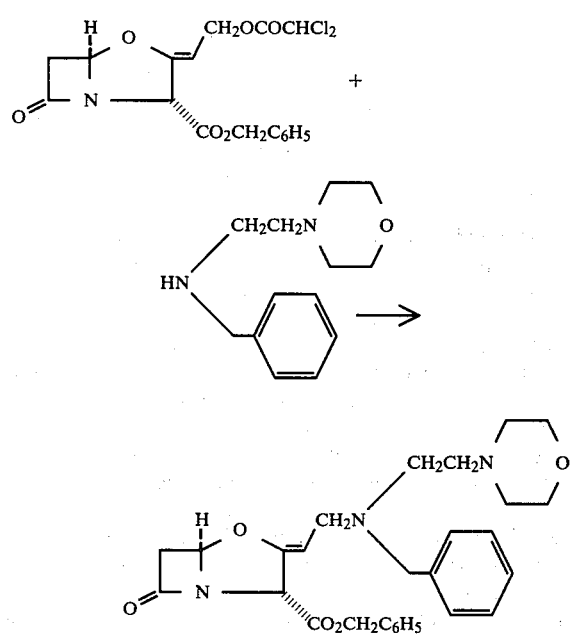

Benzyldichloroacetylclavulanate (3.76 g; 9.4 mM), in dry dimethylformamide (50 cm³) was treated with 1.9 equivalents of N-(2'-N-morpholinoethyl) benzylamine, dropwise with stirring. Stirring was continued for 1½ hours at −5°; the mixture was poured into ethyl acetate (250 cm³), washed with water (6×100 cm³), saturated to yield an oil. A portion of this crude oil (2.5 g) was chromatographed on silica eluting with methyl acetate; fractions were collected containing the title compound, Rf (SiO₂/methylacetate)=0.58. The combined fractions were evaporated to yield the title compound as an oil (0.58 g) (25%), ν(film) 1805, 1755, 1700, 1455, 1305, 1180, 1120, 1010, 745, 702 cm⁻¹; δ(CDCl₃) 2.25–2.60 (8H, m, NCH₂CH₂N and N(CH₂CH₂)₂O), 2.95 (1H, d, J 17 Hz, 6βCH), 3.20 (2H, d, J 7 Hz, 9CH₂), 3.42 (1H, dd, J 17 and 3 Hz, 6αCH), 3.48 (2H, s, NCH₂C₆H₅), 3.55–3.75 (4H, m, N(CH₂CH₂)₂O), 4.73 (1H, t, J 7 Hz, 8CH), 5.05 (1H, s, 3CH), 5.15 (2H, s, OCH₂C₆H₅), 5.61 (1H, d, J 3 Hz, 5αCH), 7.25 and 7.32 (10H, 2×s, 2×CH₂C₆H₅).

DESCRIPTION 3

Benzyl 9-N-[3'-N-(2''-pyrrolidinonyl)propyl]-N-(2'''-methyl-3'''-phenylallyl)amino deoxyclavulanate

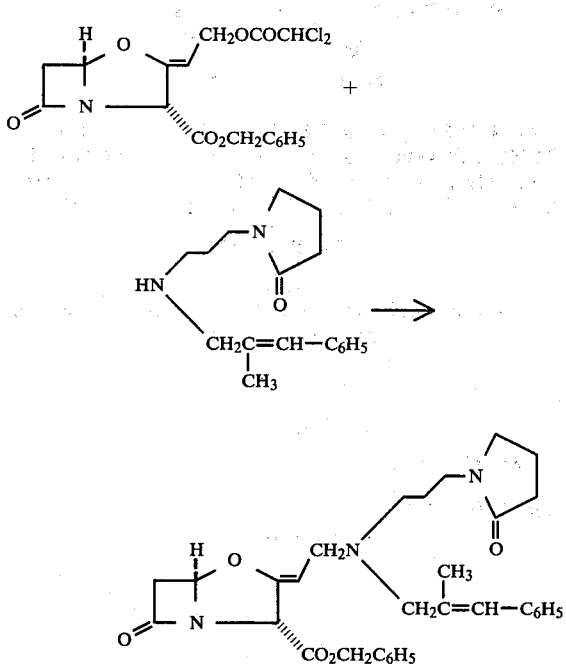

Benzyl dichloroacetylclavulanate (3.77 g; 9.42 mM) in dry dimethylformamide (50 cm³) at −5° was treated with N-[3'-N-(2''-pyrrolidinonyl)propyl]-N-(2-methyl-3-phenylallyl)amine (1.9 equivalents), and stirred at −5° for 1¾ hours. The mixture was poured into ethylacetate (250 cm³), washed with water (6×150 cm³), saturated brine (6×150 cm³), dried (anhydrous magnesium sulphate) and evaporated to an oil. This oil was chromatographed on silica eluting with methylacetate-cyclohexane (1:1) grading to neat methylacetate. Fractions were collected containing material Rf (SiO₂/methyl acetate)=0.47 (detection by aqueous potassium permanganate spray). The combined fractions were evaporated to yield the title compound as an oil, (2.30 g) (45%); ν(film) 1802, 1750, 1682, 1492, 1462, 1445, 1428, 1305, 1265, 1230, 1180, 1120, 1080, 1045, 1018, 750, 702 cm⁻¹; δ(CDCl₃) 1.45–2.15

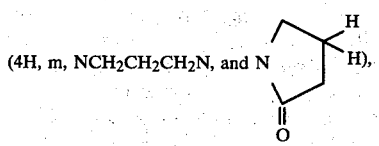
(4H, m, NCH₂CH₂CH₂N, and N ... H), 1.84 (3H, d, J 1.5 Hz, CH₂C(CH₃)=CH-C₆H₅), 2.15–2.55

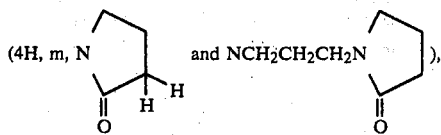

(4H, m, N...  and NCH₂CH₂CH₂N...), 2.95 (2H, s, NCH₂C(CH₃)=CH—C₆H₅), 2.96 (1H, d, J 17 Hz, 6βCH), 3.10-3.42

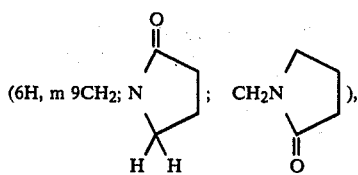

(6H, m 9CH₂; N...; CH₂N...), 3.42 (1H, dd, J 17 and 3 Hz, 6αCH), 4.71 (1H, t, J 7 Hz, 8CH), 5.06 (1H, s, 3CH), 5.18 (2H, s, CO₂CH₂C₆H₅), 5.62 (1H, d, J 3 Hz, 5αCH) 6.34 (1H, broad s,=CHC₆H₅), 7.25 and 7.33 (10H, 2×s, 2×C₆H₅).

DESCRIPTION 4

Benzyl 9-N-(3-morpholinopropyl)-N-(trans-2,3-dimethylallyl) aminodeoxy clavulanate

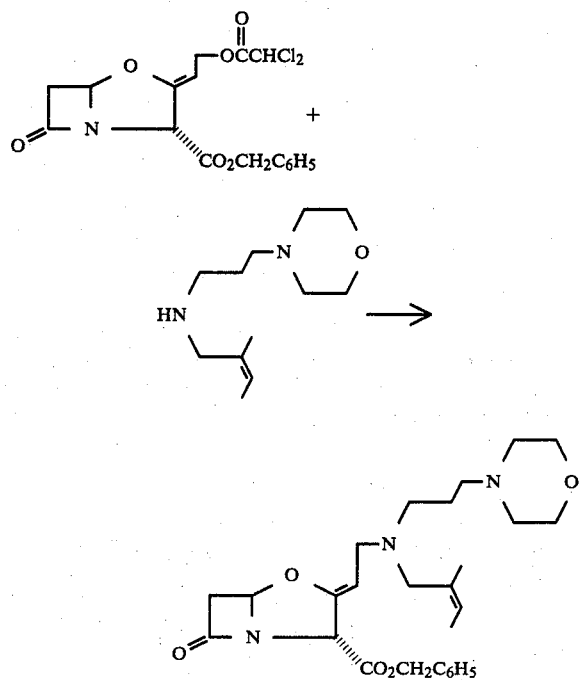

Benzyl dichloroacetylclavulanate (7.85 g; 19.6 mmol) in dimethylformamide (50 cm³) at −10° was treated with 1.9 equivalents of N-(3-morpholinopropyl)2,3-dimethylallylamine, dropwise in dimethylformamide with stirring over 5 minutes. The reaction mixture was stirred at −10° to +5° over 1½ hours when it was poured into methylacetate (250 cm³) and washed with H₂O (5×100 cm³), saturated brine (5×100 cm³) and dried (anhydrous magnesium sulphate). The crude product obtained by evaporation of the solvent was chromatographed on silica eluting with methyl acetate-ethanol (4:1), fractions were collected containing the title compound Rf (SiO₂/methylacetate-ethanol; 4:1)=0.3. Combined fractions were evaporated to afford 1.4 g of moderately pure material and 0.8 g of less pure material, the latter was rechromatographed to afford 300 mg of pure material. Total yield=1.7 g (18%) ν (film) 1800, 1747, 1692, 740, 700 cm⁻¹, δ(CDCl₃) 1.56 (8H, brs, NCH₂CH₂CH₂N, 2×—CH₃), 2.15-2.50 (8H, m, NCH₂— CH₂CH₂N(CH₂CH₂)₂O), 2.78 (2H, s, NCH₂C(CH₃)=), 2.97 (1H, d, J 17 Hz, 6αCH), 3.10 (2H, d, J 7 Hz, 9CH₂), 3.43 (1H, dd, J 17 and 3 Hz, 6αCH), 3.59-3.79 (4H, m, N (CH₂CH₂)₂O), 4.69 (1H, bt, J 7 Hz, 8CH), 5.05 (1H, bs, 3CH), 5.18 (2H, s, OCH₂C₆H₅), 5.1-5.45 (1H, bm,=CH(CH₃)), 5.62 (1H, d, J 3 Hz, 5αCH), 7.33 (5H, s, CH₂C₆H₅).

EXAMPLE 1

9-N-(2'-N-Morpholinoethyl)aminodeoxyclavulanic acid

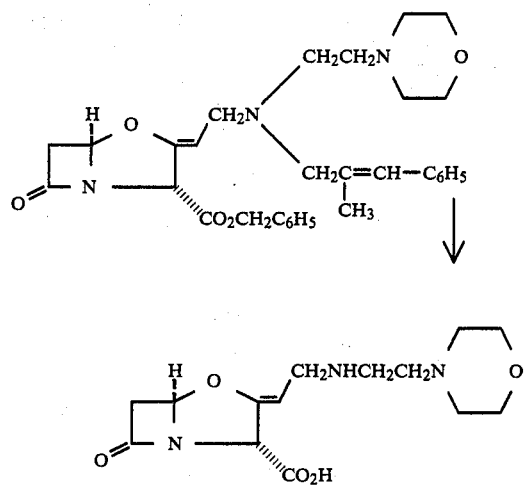

Benzyl 9-N-(2'-N-morpholinoethyl)-N-(2"-methyl-3"-phenylallyl)aminodeoxyclavulanate (1.23 g; 2.32 mmol in tetrahydrofuran-ethanol (1:1; 50 cm³) was hydrogenolysed at atmospheric pressure in the presence of 0.4 g palladium on carbon (10%, which had been prehydrogenated for 15 minutes), for 1½ hours. The catalyst was filtered off and washed with ethanol (20 cm³) then with aqueous ethanol (150 cm). This aqueous washing was evaporated to yield a white crystalline solid. This solid was slurried in cold ethanol and filtered off, washed with a little cold ethanol and dried in vacuo to afford the title compound (0.128 g). The filtered catalyst was shaken with warm aqueous ethanol and filtered. The clear filtrate was evaporated to afford a further amount of the title compound (0.093 g) as a white crystalline solid. Total yield=220 mg (31%), Rf (SiO₂/butanol-propan-2-ol-water; 7:7:6)=0.16, ν(Nujol) 1800, 1695, 1605 (broad) cm⁻¹; ν(KBr) (3680-3040), (3040-2890), 2820, 2740 (broad), 2480 (broad), 2450 (broad), 1790, 1692, 1615, 1579, 1476, 1460, 1400, 1334, 1300, 1263, 1186, 1112, 1085, 1073, 1045, 1013, 973, 928, 913, 897, 880, 870, 852, 807, 786, 756 cm⁻¹; δ(D₂O) 2.37-2.77 (6H, m, N(CH₂CH₂)₂O and CHN(CH₂CH₂)₂O), 3.07 (1H, d J 17 Hz, 6βCH), 3.13 (2H, t, J 6 Hz, NCH₂CH₂N(CH₂ CH₂)₂O), 3.56 (1H, dd, J 17 and 3 Hz, 6αCH), 3.52-3.82 (6H, m, 9CH₂ and N(CH₂CH₂O), 4.77 (1H, t, J 7 Hz, 8CH), 4.98 (1H, s, 3CH), 5.74 (1H, d, J 3 Hz, 5αCH).

Demonstration of Effectiveness

By a standard microtitre technique the MIC values for ampicillin alone, ampicillin and 9-N-(2-N-morpholinoethyl)aminodeoxyclavulanic acid and 9-N-(2-N-morpholinoethyl)aminodeoxyclavulanic acid alone were determined.

MIC μg/ml (dilution in tryptone soy broth)

|  | Staph. Aureus Russell | Kleb Aergenes E70 | E. Coli JT39 |
|---|---|---|---|
| Ampicillin alone | 1000 | 1000 | >2000 |
| Ampicillin + inhibitor at |  |  |  |
| 1 μg/ml | 0.3 | 25 | 62 |
| 5 μg/ml | <0.01 | 3.1 | 16 |
| Inhibitor alone | 16 | 500 | 62 |

Antibacterial activity of 9-N-(2-N-morpholinoethyl)aminodeoxyclavulanic acid

| Staph. aureus Russell | 5.0 |
|---|---|
| Strep. pyogenes | 2.5 |
| Strep. pnenmoniae | 10 |

EXAMPLE 2

9-N[3'-N-(2"-Pyrrolidinonyl)propyl]aminodeoxyclavulanic acid

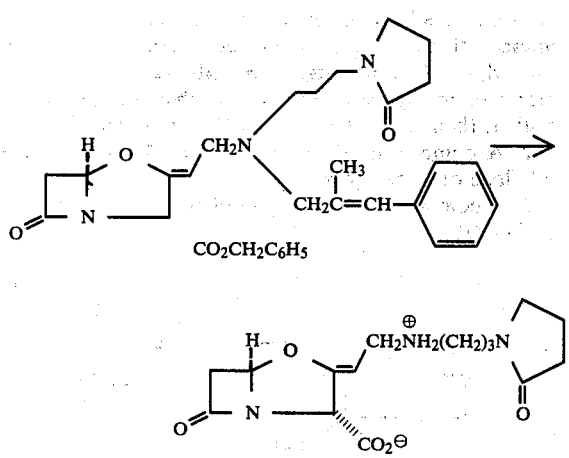

Benzyl 9-N-[3'-N-(2"-pyrrolidinonyl)propyl]-N-(2"-methyl-3'"-phenylallyl) aminodeoxyclavulanate (2.2 g; 4.05 mM) in ethanol (50 cm³) was hydrogenolysed at atmospheric pressure in the presence of 0.66 g Palladium on carbon (10%; prehydrogenated for 15 minutes) for 1¼ hours. The catalyst was filtered off and washed with aqueous ethanol (100 cm³). The filtrate was evaporated, acetonitrile added (30 cm³) and cooled (0°), a white crystalline solid formed which was filtered off, washed with a little cold acetonitrile and dried to yield the title compound (0.495 g) (38%), Rf (SiO₂/butanol-propan-2-ol-water; 7:7:6)=0.20 (detection by aqueous potassium permanganate spray), (Nujol) 3550, 3470, 1805, 1690, 1665, 1600, 1308, 1195, 1122, 1105, 1070, 1050, 1025, 1007, 925, 900, 852, 820, 800, 790, 762 cm⁻¹; ν(KBr), (3700–3130), (3130–2495), (2495–2500), (2500–2200), 1792, 1687, 1658, 1590, 1465, 1435, 1390, 1370, 1362, 1333, 1300, 1270, 1192, 1185, 1130, 1100, 1043, 1020, 1000, 932, 920, 895, 850, 815, 797, 785, 758 cm⁻¹; δ(D₂O) 1.70–2.55

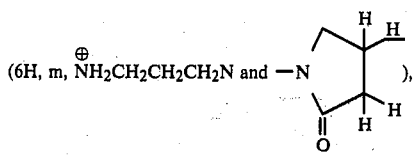

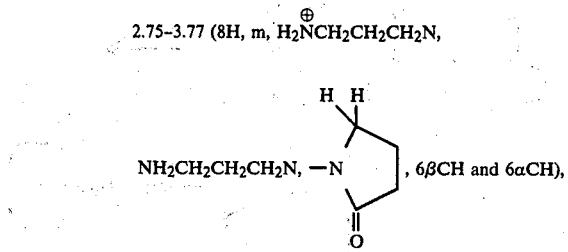

3.70 (2H, d, J 7 Hz, 9C$\underline{H}_2$), 4.77 (1H, t, J 7 Hz, 8C$\underline{H}$), 4.95 (1H, s, 3C$\underline{H}$), 5.72 (1H, d, J 3 Hz, 5αC$\underline{H}$).

Demonstration of Effectiveness

By a standard microtitre technique the MIC values for ampicillin alone, ampicillin and 9-N-[3'-N-(2"-pyrrolidinoyl)propyl]aminodeoxyclavulanic acid and 9-N[3'-N-(2"-pyrrolidinoyl)propyl]aminodeoxyclavulanic acid alone were determined.

MIC μg/ml (dilution in tryptone soy broth)

|  | Staph Aureus Russell | Kleb Aerogenes E 70 | E. Coli JT39 |
|---|---|---|---|
| Ampicillin alone | 1000 | 1000 | >2000 |
| Ampicillin and inhibitor at 1 μg/ml | 0.62 | 6.2 | 62 |
| Ampicillin and inhibitor at 5 μg/ml | 0.08 | 6.2 | 8.0 |
| Inhibitor alone | 16 | 500 | 62 |

Antibacterial activity of 9-N-[3'-N-(2"-pyrrolidinonyl)propyl]aminodeoxyclavulanic acid Dilution in blood agar-heavy inoculum

|  | MIC μg/ml |
|---|---|
| Staph. aureus Oxford | 5 |
| Staph. aureus Russell | 5.0 |
| Strep. pyogenes | 1.25 |
| Strep. pneumoniae | 5 |

EXAMPLE 3

9-N-(3'-Morpholinopropyl)amino deoxyclavulanic acid

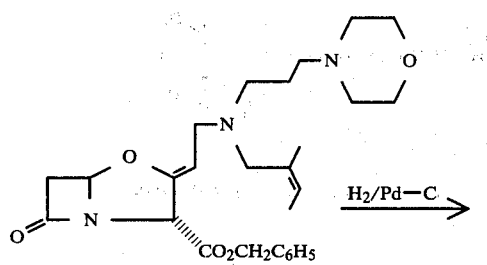

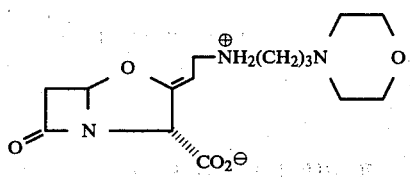

Benzyl 9-N-(3-morpholinopropyl)-N-(2,3-dimethylallyl)amino deoxyclavulanate (300 mg; 0.6 mmol) in ethanol (15 cm³) and water (2 cm³) was hydrogenolysed at atmospheric pressure in the presence of 10% palladium on carbon (100 mg) which had been prehydrogenated for 15 minutes for 1¼ hours. The catalyst was filtered off and washed with aqueous ethanol then evaporated to an oil. Ethanol was added and allowed to stand at room temperature. Crystals slowly formed and these were filtered off cold and washed with cold ethanol. Drying afforded 57 mg (29%) of the title compound as a colourless crystalline solid. Rf (SiO₂/methylacetate-ethanol-water; 1:1:1)=0.15 (detection by aqueous potassium permanganate spray). ν (nujol) 1800, 1785 (shoulder) 1690, 1615, 1560, 1302, 1287, 1185, 1110, 1045, 1017, 1005, 995, 890, 750 cm⁻¹. The ¹H nuclear magnetic resonance spectrum was consistent with the desired compound.

What we claim is:

1. A compound of the formula (II):

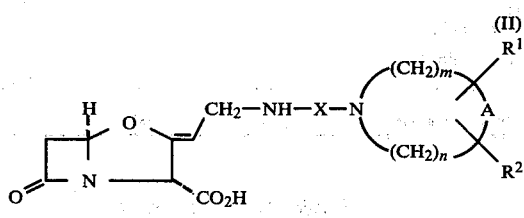

(II)

a pharmaceutically acceptable salt thereof, an ester thereof of the formula:

wherein A₁ is alkyl of 1 to 6 carbon atoms unsubstituted or monosubstituted by alkoxy of 1 to 7 carbon atoms or alkanoyloxy of 1 to 7 carbon atoms, or A₁ is a moiety of the sub-formula (a):

     (a)

wherein A₂ is alkenyl of up to 5 carbon atoms, alkynyl of up to 5 carbon atoms, or phenyl unsubstituted or mono-substituted by a fluorine, chlorine or bromine atom or by a nitro, alkyl of up to 4 carbon atoms or alkoxyl of up to 4 carbon atoms moiety; and A₃ is hydrogen, alkyl of up to 4 carbon atoms or phenyl unsubstituted or mono-substituted by a fluorine, chlorine or bromine atom or by a nitro, alkyl of up to 4 carbon atoms or alkoxyl of up to 4 carbon atoms moiety or A₁ is ethoxycarbonyloxymethyl, methoxycarbonyloxyethyl, ethoxycarbonyloxyethyl, or a moiety of the formula (b), (c) or (d):

wherein A₄ is hydrogen or methyl, A₅ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formulae (c) and (d) is also alkyl of up to 4 carbon atoms; or A₄ and A₅ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety, or an acid addition salt of said ester wherein X is alkylene of 1 to 6 carbon atoms; m is 1, 2, or 3; n is 1, 2 or 3; A is oxygen or sulphur; R¹ is hydrogen, oxo, alkyl of 1 to 6 carbon atoms, alkoxy of 1 to 6 carbon atoms, hydroxy or phenyl; and R² is hydrogen, oxo, alkyl of 1 to 6 carbon atoms or phenyl; with the proviso that if m and n are both 1, then A is —CH₂— and R² is not oxo.

2. A compound according to claim 1 wherein X is ethylene or trimethylene.

3. A compound according to claim 1 or 2 of the formula (III):

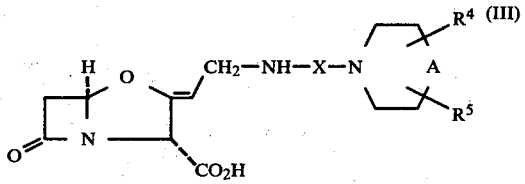

a pharmaceutically acceptable salt thereof, an ester thereof of the formula:

wherein A₁ is alkyl of 1 to 6 carbon atoms unsubstituted or monosubstituted by alkoxy of 1 to 7 carbon atoms or alkanoyloxy of 1 to 7 carbon atoms, or A₁ is a moiety of the sub-formula (a):

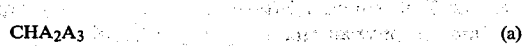     (a)

wherein A₂ is alkenyl of up to 5 carbon atoms, alkynyl of up to 5 carbon atoms, or phenyl unsubstituted or mono-substituted by a fluorine, chlorine or bromine atom or by a nitro, alkyl of up to 4 carbon atoms or alkoxyl of up to 4 carbon atoms moiety; and A₃ is hydrogen, alkyl of up to 4 carbon atoms or phenyl unsubstituted or mono-substituted by a fluorine, chlorine or bromine atom or by a nitro, alkyl of up to 4 carbon atoms or alkoxyl of up to 4 carbon atoms moiety or A₁ is ethoxycarbonyloxymethyl, methoxycarbonyloxyethyl, ethoxycarbonyloxyethyl, or a moiety of the formula (b), (c) or (d):

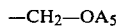 (b)

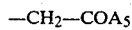 (c)

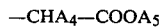 (d)

wherein A₄ is hydrogen or methyl, A₅ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formulae (c) and (d) is also alkyl of up to 4 carbon atoms; or A₄ and A₅ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety, or an acid addition salt of said ester wherein R⁴ and R⁵ are independently hydrogen or alkyl of 1 to 6 carbon atoms.

4. A compound of the formula (IV):

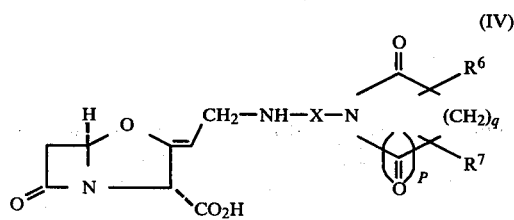

a pharmaceutically acceptable salt thereof, an ester thereof or an acid additional salt of said ester wherein P is zero or 1, q is 2, 3 or 4; R⁶ is hydrogen, alkoxy of 1 to 6 carbon atoms, alkyl of 1 to 6 carbon atoms, hydroxy or phenyl; and R⁷ is hydrogen or alkyl of 1 to 6 carbon atoms.

5. A compound according to claim 1 in zwitterionic form.

6. A compound according to claim 1 wherein A₁ is methyl, ethyl, n-propyl, n-butyl, allyl, 2-methylallyl, CH₂—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, phthalidyl, dimethoxyphthalidyl, benzyl, methoxybenzyl, ethoxybenzyl, nitrobenzyl or chlorobenzyl.

7. A compound according to claim 1 wherein A₁ is methyl, ethyl, propyl, methoxy, acetoxymethyl, acetoxyethyl, phthalidyl, ethoxycarbonyloxymethyl or α-ethoxycarbonyloxyethyl; A₂ is phenyl or methoxyphenyl; and A₃ is hydrogen.

8. A compound according to claim 1 wherein A₁ is of the formula (b), (c) or (d):

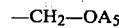 (b)

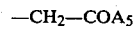 (c)

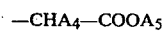 (d)

wherein A₄ is hydrogen or methyl, A₅ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formula (c) and (d) A₅ is also alkyl of up to 4 carbon atoms; or A₄ and A₅ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety.

9. A compound according to claim 8 wherein the moiety of the formula (b) is —CH₂—OA₅ wherein A₅ is phenyl or benzyl.

10. A compound according to claim 8 wherein the moiety of the formula (c) is —CH₂—CO₂A₅ wherein A₅ is methyl, ethyl, propyl, butyl, phenyl or benzyl.

11. A compound according to claim 8 wherein the moiety of the formula (d) is —CH₂—CO₂A₅ wherein A₅ is methyl, ethyl, propyl, butyl, phenyl or benzyl.

12. A compound according to claim 8 wherein the moiety of the formula (d) is —CH(CH₃)—CO₂A₅ wherein A₅ is methyl, ethyl, propyl, butyl, phenyl or benzyl.

13. A compound according to claim 1 wherein X is methylene, ethylene, isopropylene, trimethylene, tetramethylene, pentamethylene or hexamethylene.

14. A compound according to claim 1 wherein m is 1 or 2.

15. A compound according to claim 1 wherein m is 2.

16. A compound according to claim 1 wherein n is 1 or 2.

17. A compound according to claim 1 wherein m+n is 3.

18. A compound according to claim 1 wherein m+n is 4.

19. A compound according to claim 1 wherein A is oxygen or sulphur.

20. A compound according to claim 1 wherein A is oxygen.

21. A compound according to claim 1 wherein A is —CH₂—.

22. A compound according to claim 1 wherein R¹ is hydrogen, oxo, methyl, ethyl, propyl or butyl.

23. A compound according to claim 1 wherein R¹ is hydrogen, oxo, methyl or ethyl.

24. A compound according to claim 1 wherein R² is hydrogen, oxo, methyl, ethyl, propyl or butyl.

25. A compound according to claim 1 wherein R² is hydrogen, oxo, methyl or ethyl.

26. A compound according to claim 3 wherein A is oxygen and R⁴ and R⁵ are each hydrogen, methyl, ethyl or propyl.

27. A compound according to claim 3 wherein X is ethylene, or trimethylene.

28. A compound according to claim 4 wherein p is zero and q is 2, 3 or 4.

29. A compound according to claim 28 wherein q is 3.

30. A compound according to claim 4 wherein R⁶ is hydrogen, alkyl of 1 to 3 carbon atoms, alkoxy of 1 to 3 carbon atoms, phenyl or hydroxy.

31. A compound according to claim 4 wherein R⁶ is hydrogen, alkyl of 1 to 3 carbon atoms, or phenyl.

32. A compound according to claim 4 wherein R⁶ is hydrogen.

33. A compound according to claim 4 wherein R⁷ is hydrogen, alkyl of 1 to 3 carbon atoms, or phenyl.

34. A compound according to claim 4 wherein $R^7$ is hydrogen.

35. A compound according to claim 1 in the form of a pharmaceutically acceptable acid addition salt wherein said salt is the hydrochloride, phosphate, sulphate, methanesulphanate, toluenesulphanate, citrate, maliate, acetate, lactate, tartrate, propionate or succinate.

36. The compound according to claim 1 which is 9-N-(2'-Morpholinoethyl)aminodeoxyclavulanic acid.

37. The compound according to claim 1 which is 9-N-(3'-Morpholinopropyl)aminodeoxyclavulanic acid.

38. The compound according to claim 1 which is 9-N-(3'-N-(2'-Pyrrolidino)propylaminodeoxyclavulanic acid.

39. A pharmaceutical composition useful for treating bacterial infections in mammals including humans which comprises an antibacterially effective amount of a compound of the formula (II):

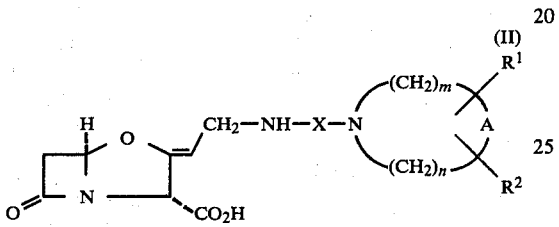

a pharmaceutically acceptable salt thereof, an ester thereof of the formula:

wherein $A_1$ is alkyl of 1 to 6 carbon atoms unsubstituted or mono-substituted by alkoxy of 1 to 7 carbon atoms or alkanoyloxy of 1 to 7 carbon atoms, or $A_1$ is a moiety of the sub-formula (a):

CHA$_2$A$_3$ (a)

wherein $A_2$ is alkenyl of up to 5 carbon atoms, alkynyl of up to 5 carbon atoms, or phenyl unsubstituted or mono-substituted by a fluorine, chlorine or bromine atom or by a nitro, alkyl of up to 4 carbon atoms or alkoxyl of up to 4 carbon atoms moiety; and $A_3$ is hydrogen, alkyl of up to 4 carbon atoms or phenyl unsubstituted or mono-substituted by a fluorine, chlorine or bromine atom or by a nitro, alkyl of up to 4 carbon atoms or alkoxyl of up to 4 carbon atoms moiety or $A_1$ is ethoxycarbonyloxymethyl, methoxycarbonyloxyethyl, ethoxycarbonyloxyethyl, or a moiety of the formula (b), (c) or (d):

—CH$_2$—OA$_5$ (b)

—CH$_2$—COA$_5$ (c)

—CHA$_4$—COOA$_5$ (d)

wherein $A_4$ is hydrogen or methyl, $A_5$ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formulae (c) and (d) is also alkyl of up to 4 carbon atoms; or $A_4$ and $A_5$ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety, or an acid addition salt of said ester wherein X is alkylene of 1 to 6 carbon atoms; m is 1, 2 or 3; n is 1, 2 or 3; A is oxygen or sulphur; $R^1$ is hydrogen, oxo, alkyl of 1 to 6 carbon atoms, alkoxy of 1 to 6 carbon atoms, hydroxy or phenyl; and $R^2$ is hydrogen, oxo, alkyl of 1 to 6 carbon atoms or phenyl, with the proviso that if m and n are both 1 then A is —CH$_2$— and $R^2$ is not oxo as the sole antibacterial agent, in combination with a pharmaceutically acceptable carrier.

40. A method of treating bacterial infections in mammals including humans which comprises administering to such a mammal in need thereof an antibacterially effective amount of a compound of the formula (II):

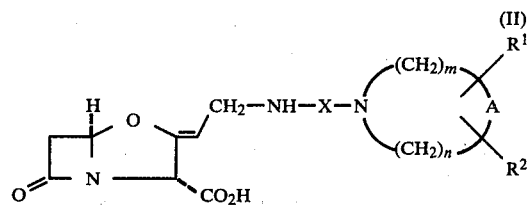

a pharmaceutically acceptable salt thereof, an ester thereof of the formula:

wherein $A_1$ is alkyl of 1 to 6 carbon atoms unsubstituted or mono-substituted by alkoxy of 1 to 7 carbon atoms or alkanoyloxy of 1 to 7 carbon atoms, or $A_1$ is a moiety of the sub-formula (a):

CHA$_2$A$_3$ (a)

wherein $A_2$ is alkenyl of up to 5 carbon atoms, alkynyl of up to 5 carbon atoms, or phenyl unsubstituted or mono-substituted by a fluorine, chlorine or bromine atom or by a nitro, alkyl of up to 4 carbon atoms or alkoxyl of up to 4 carbon atoms moiety; and $A_3$ is hydrogen, alkyl of up to 4 carbon atoms or phenyl unsubstituted or mono-substituted by a fluorine, chlorine or bromine atom or by a nitro, alkyl of up to 4 carbon atoms or alkoxyl of up to 4 carbon atoms moiety or $A_1$ is ethoxycarbonyloxymethyl, methoxycarbonyloxyethyl, ethoxycarbonyloxyethyl, or a moiety of the formula (b), (c) or (d):

—CH$_2$—OA$_5$ (b)

—CH$_2$—COA$_5$ (c)

—CHA$_4$—COOA$_5$ (d)

wherein $A_4$ is hydrogen or methyl, $A_5$ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formulae (c) and (d) is also alkyl of up to 4 carbon atoms; or $A_4$ and $A_5$ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety, or an acid addition salt of said ester wherein X is alkylene of 1 to 6 carbon atoms; m is 1, 2 or 3; n is 1, 2 or 3; A is oxygen or sulphur; $R^1$ is hydrogen, oxo, alkyl of 1 to 6 carbon atoms, alkoxy of 1 to 6 carbon atoms, hydroxy or phenyl; and $R^2$ is hydrogen, oxo, alkyl of 1 to 6 carbon atoms or phenyl, with the proviso that if m and n are both 1 then A is —CH$_2$— and $R^2$ is not oxo in combination with a pharmaceutically acceptable carrier.

41. A method according to claim 40 wherein $A_1$ is methyl, ethyl, n-propyl, n-butyl, allyl, 2-methylallyl, CH$_2$—C═CH$_2$, methoxymethyl, acetoxymethyl, propionoxymethyl, pivaloyloxymethyl, ethoxycarbonyloxymethyl, methoxycarbonyloxyethyl, ethoxycarbonyloxyethyl, phthalidyl, dimethoxyphthalidyl, benzyl, methoxybenzyl, ethoxybenzyl, nitrobenzyl or chlorobenzyl.

42. A method according to claim 40 wherein $A_1$ is methyl, ethyl, propyl, methoxy, acetoxymethyl, acetoxyethyl, phthalidyl, ethoxycarbonyloxymethyl or α-ethoxycarbonyloxyethyl; $A_2$ is phenyl or methoxyphenyl; and $A_3$ is hydrogen.

43. A composition according to claim 39 wherein X is ethylene or trimethylene.

44. A composition according to claim 39 wherein the compound is of the formula (III):

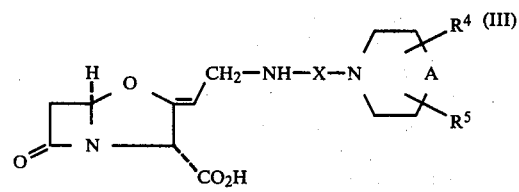

a pharmaceutically acceptable salt thereof, an ester thereof of the formula:

wherein $A_1$ is alkyl of 1 to 6 carbon atoms unsubstituted or mono-substituted by alkoxy of 1 to 7 carbon atoms or alkanoyloxy of 1 to 7 carbon atoms, or $A_1$ is a moiety of the sub-formula (a):

         (a)

wherein $A_2$ is alkenyl of up to 5 carbon atoms, alkynyl of up to 5 carbon atoms, or phenyl unsubstituted or mono-substituted by a fluorine, chlorine or bromine atom or by a nitro, alkyl of up to 4 carbon atoms or alkoxyl of up to 4 carbon atoms moiety; and $A_3$ is hydrogen, alkyl of up to 4 carbon atoms or phenyl unsubstituted or mono-substituted by a fluorine, chlorine or bromine atom or by a nitro, alkyl of up to 4 carbon atoms or alkoxyl of up to 4 carbon atoms moiety or $A_1$ is ethoxycarbonyloxymethyl, methoxycarbonyloxyethyl, ethoxycarbonyloxyethyl, or a moiety of the formula (b), (c) or (d):

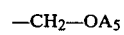         (b)

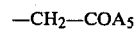         (c)

—CHA$_4$—COOA$_5$         (d)

wherein $A_4$ is hydrogen or methyl, $A_5$ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formulae (c) and (d) is also alkyl of up to 4 carbon atoms; or $A_4$ and $A_5$ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety, or an acid addition salt of said ester wherein X is alkylene of 1 to 6 carbon atoms, A is oxygen or sulphur and $R^4$ and $R^5$ are independently hydrogen or alkyl of 1 to 6 carbon atoms.

45. A pharmaceutical composition useful for treating bacterial infections in mammals including humans which comprises an antibacterially effective amount of a compound of the formula (IV):

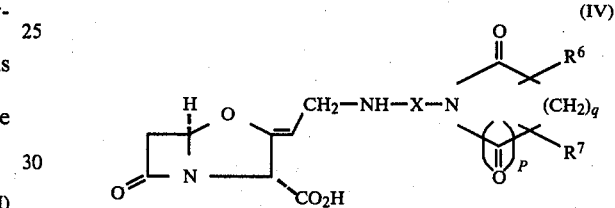

a pharmaceutically acceptable salt thereof, a pharmaceutically acceptable ester thereof or an acid addition salt of said ester wherein P is zero or 1, q is 2, 3 or 4; $R^6$ is hydrogen, alkoxy of 1 to 6 carbon atoms, alkyl of 1 to 6 carbon atoms, hydroxy of phenyl; and $R^7$ is hydrogen or alkyl of 1 to 6 carbon atoms, in combination with a pharmaceutically acceptable carrier.

46. A composition according to claim 39 wherein X is methylene, ethylene, isopropylene, trimethylene, tetramethylene, pentamethylene or hexamethylene.

47. A composition according to claim 39 wherein m is 1 or 2.

48. A composition according to claim 39 wherein m is 2.

49. A composition according to claim 39 wherein n is 1 or 2.

50. A composition according to claim 39 wherein m+n is 3.

51. A composition according to claim 39 wherein m+n is 4.

52. A composition according to claim 39 wherein A is sulphur.

53. A composition according to claim 39 wherein A is oxygen.

54. A composition according to claim 39 wherein A is —CH$_2$—.

55. A composition according to claim 39 wherein $R^1$ is hydrogen, oxo, methyl, ethyl, propyl or butyl.

56. A composition according to claim 39 wherein $R^1$ is hydrogen, oxo, methyl or ethyl.

57. A composition according to claim 39 wherein $R^2$ is hydrogen, oxo, methyl, ethyl, propyl or butyl.

58. A composition according to claim 39 wherein $R^2$ is hydrogen, oxo, methyl or ethyl.

59. A composition according to claim 44 wherein A is oxygen and $R^4$ and $R^5$ are each hydrogen, methyl, ethyl or propyl.

60. A composition according to claim 44 wherein X is ethylene or trimethylene.

61. A composition according to claim 45 wherein p is zero and q is 2, 3 or 4.

62. A composition according to claim 61 wherein q is 3.

63. A composition according to claim 45 wherein $R^6$ is hydrogen, alkyl of 1 to 3 carbon atoms, alkoxy of 1 to 3 carbon atoms, phenyl or hydroxy.

64. A composition according to claim 45 wherein $R^6$ is hydrogen, alkyl of 1 to 3 carbon atoms, or phenyl.

65. A composition according to claim 45 wherein $R^6$ is hydrogen.

66. A composition according to claim 45 wherein $R^7$ is hydrogen, alkyl of 1 to 3 carbon atoms, or phenyl.

67. A composition according to claim 45 wherein $R^7$ is hydrogen.

68. A method according to claim 40 wherein $A_1$ is of the formula (b), (c) or (d):

$$-CH_2-OA_5 \quad (b)$$

$$-CH_2-COA_5 \quad (c)$$

$$-CHA_4-COOA_5 \quad (d)$$

wherein $A_4$ is hydrogen or methyl, $A_5$ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formula (c) and (d) $A_5$ is also alkyl of up to 4 carbon atoms; or $A_4$ and $A_5$ together with the —CH—O—CO— moiety form an orthophenylene moiety which is unsubstituted or substituted by one or two alkyl or alkoxyl moieties of up to 3 carbon atoms, or by a fluorine, chlorine or bromine atom or a nitro moiety.

69. A composition according to claim 39 wherein the compound is in zwitterionic form.

70. A method according to claim 68 wherein the moiety of the formula (b) is —$CH_2$—$OA_5$ wherein $A_5$ is methyl, ethyl, propyl, butyl, phenyl or benzyl.

71. A composition according to claim 39 wherein $A_1$ is methyl, ethyl, n-propyl, n-butyl, allyl, 2-methylallyl, $CH_2$—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, phthalidyl, dimethoxyphthalidyl, benzyl, methoxybenzyl, ethoxybenzyl, nitrobenzyl or chlorobenzyl.

72. A composition according to claim 39 wherein $A_1$ is methyl, ethyl, propyl, methoxy, acetoxymethyl, acetoxymethyl, phthalidyl, ethoxycarbonyloxymethyl or α-ethoxycarbonyloxyethyl; $A_2$ is phenyl or methoxyphenyl; and $A_3$ is hydrogen.

73. A composition according to claim 39 wherein $A_1$ is of the formula (b), (c) or (d):

$$-CH_2-OA_5 \quad (b)$$

$$-CH_2-COA_5 \quad (c)$$

$$-CHA_4-COOA_5 \quad (d)$$

wherein $A_4$ is hydrogen or methyl, $A_5$ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formula (c) and (d) $A_5$ is also alkyl of up to 4 carbon atoms; or $A_5$ and $A_5$ together with the —CH—O—CO— moiety form an orthophenylene moiety which is unsubstituted or substituted by one or two alkyl or alkoxyl moieties of up to 3 carbon atoms, or by a fluorine, chlorine or bromine atom or a nitro moiety.

74. A composition according to claim 73 wherein the moiety of the formula (b) is —$CH_2$—$OA_5$ wherein $A_5$ is phenyl or benzyl.

75. A composition according to claim 73 wherein the moiety of the formula (c) is —$CH_2$—CO—$A_5$ wherein $A_5$ is methyl, ethyl, propyl, butyl, phenyl or benzyl.

76. A composition according to claim 73 wherein the moiety of the formula (d) is —$CH_2$—$CO_2A_5$ wherein $A_5$ is methyl, ethyl, propyl, butyl, phenyl or benzyl.

77. A composition according to claim 73 wherein the moiety of the formula (d) is —$CH(CH_3)$—$CO_2A_5$ wherein $A_5$ is methyl, ethyl, propyl, butyl, phenyl or benzyl.

78. A method according to claim 68 wherein the moiety of the formula (b) is —$CH_2$—$OA_5$ wherein $A_5$ is phenyl or benzyl.

79. A composition according to claim 39 wherein the compound is in the form of a pharmaceutically acceptable acid addition salt wherein said salt is the hydrochloride, phosphate, sulphate, methanesulphanate, toluenesulphanate, citrate, maliate, acetate, lactate, tartrate, propionate or succinate.

80. A composition according to claim 39 for the treatment of a bacterial infection caused by Staph.aureus which composition contains an amount of said compound sufficient to be effective against the Staph.aureus infection.

81. A composition according to claim 39 for the treatment of a bacterial infection caused by Klebsiella aerogenes which composition contains an amount of said compound sufficient to be effective against the Klebsiella aerogenes infection.

82. A composition according to claim 39 for the treatment of a bacterial infection caused by Escherichia coli which composition contains an amount of said compound sufficient to be effective against the Escherichia coli infection.

83. A composition according to claim 39 for the treatment of a bacterial infection caused by Proteus sp which composition contains an amount of said compound sufficient to be effective against the Proteus sp infection.

84. A method according to claim 40 wherein X is ethylene or trimethylene.

85. A method according to claim 39 wherein the compound is of the formula (III):

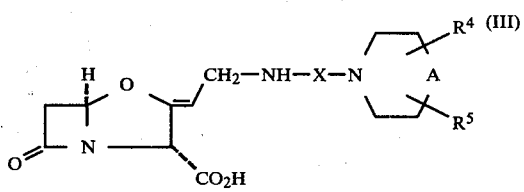

a pharmaceutically acceptable salt thereof, an ester thereof of the formula:

wherein $A_1$ is alkyl of 1 to 6 carbon atoms unsubstituted or monosubstituted by alkoxy of 1 to 7 carbon atoms or alkanoyloxy of 1 to 7 carbon atoms, or $A_1$ is a moiety of the sub-formula (a):

   (a)

wherein $A_2$ is alkenyl of up to 5 carbon atoms, alkynyl of up to 5 carbon atoms, or phenyl unsubstituted or mono-substituted by a fluorine, chlorine or bromine atom or by a nitro, alkyl of up to 4 carbon atoms or alkoxyl of up to 4 carbon atoms moiety; and $A_3$ is hydrogen, alkyl of up to 4 carbon atoms or phenyl unsubstituted or mono-substituted by a fluorine, chlorine or bromine atom or by a nitro, alkyl of up to 4 carbon atoms or alkoxyl of up to 4 carbon atoms moiety or $A_1$ is ethoxycarbonyloxymethyl, methoxycarbonyloxyethyl, ethoxycarbonyloxyethyl, or a moiety of the formula (b), (c) or (d):

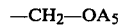   (b)

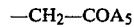   (c)

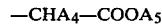   (d)

wherein $A_4$ is hydrogen or methyl, $A_5$ is phenyl or benzyl, either of which is unsubstituted or mono-substituted by 1 or 2 alkyl or alkoxyl moieties of up to 3 carbon atoms or either of which is substituted by a fluorine, chlorine or bromine atom or a nitro moiety and in formulae (c) and (d) is also alkyl of up to 4 carbon atoms; or $A_4$ and $A_5$ together with the —CH—O—CO moiety form an orthophenylene moiety which is unsubstituted or substituted by one or two alkyl or alkoxyl moieties of up to 3 carbon atoms, or by a fluorine, chlorine or bromine atom or a nitro moiety, or an acid addition salt of said ester wherein X is alkylene of 1 to 6 carbon atoms, A is oxygen or sulphur and $R^4$ and $R^5$ are independently hydrogen or alkyl of 1 to 6 carbon atoms.

86. A method of treating bacterial infections in mammals including humans which comprises an antibacterially effective amount of a compound of the formula (IV):

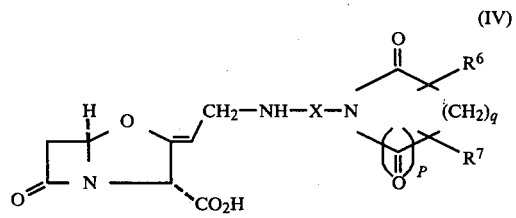   (IV)

a pharmaceutically acceptable salt thereof, a pharmaceutically acceptable ester thereof or an acid addition salt of said ester wherein P is zero or 1, q is 2, 3 or 4; $R^6$ is hydrogen, alkoxy of 1 to 6 carbon atoms, alkyl of 1 to 6 carbon atoms, hydroxy or phenyl; and $R^7$ is hydrogen or alkyl of 1 to 6 carbon atoms.

87. A method according to claim 40 wherein X is methylene, ethylene, isopropylene, trimethylene, tetramethylene, pentamethylene or hexamethylene.

88. A method according to claim 40 wherein m is 1 or 2.

89. A method according to claim 40 wherein m is 2.

90. A method according to claim 40 wherein n is 1 or 2.

91. A method according to claim 40 wherein m+n is 3.

92. A method according to claim 40 wherein m+n is 4.

93. A method according to claim 40 wherein A is sulphur.

94. A method according to claim 40 wherein A is oxygen.

95. A method according to claim 40 wherein A is —$CH_2$—.

96. A method according to claim 40 wherein $R^1$ is hydrogen, oxo, methyl, ethyl, propyl or butyl.

97. A method according to claim 40 wherein $R^1$ is hydrogen, oxo, methyl or ethyl.

98. A method according to claim 40 wherein $R^2$ is hydrogen, oxo, methyl, ethyl, propyl or butyl.

99. A method according to claim 40 wherein $R^2$ is hydrogen, oxo, methyl or ethyl.

100. A method according to claim 85 wherein A is oxygen and $R^4$ and $R^5$ are each hydrogen, methyl, ethyl or propyl.

101. A method according to claim 85 wherein X is ethylene or trimethylene.

102. A method according to claim 86 wherein p is zero and q is 2, 3 or 4.

103. A method according to claim 102 wherein q is 3.

104. A method according to claim 86 wherein $R^6$ is hydrogen, alkyl of 1 to 3 carbon atoms, alkoxy of 1 to 3 carbon atoms, phenyl or hydroxy.

105. A method according to claim 86 wherein $R^6$ is hydrogen, alkyl of 1 to 3 carbon atoms, or phenyl.

106. A method according to claim 86 wherein $R^6$ is hydrogen.

107. A method according to claim 86 wherein $R^7$ is hydrogen, alkyl of 1 to 3 carbon atoms, or phenyl.

108. A method according to claim 86 wherein $R^7$ is hydrogen.

109. A method according to claim 68 wherein the moiety of the formula (d) is —$CH_2$—$CO_2A_5$ wherein $A_5$ is methyl, ethyl, propyl, butyl, phenyl or benzyl.

110. A method according to claim 40 wherein the compound is in zwitterionic form.

111. A method according to claim 40 wherein the compound is in the form of a pharmaceutically acceptable acid addition salt wherein said salt is the hydrochloride, phosphate, sulphate, methanesulphanate, toluenesulphanate, citrate, maliate, acetate, lactate, tartrate, propionate or succinate.

112. A method according to claim 40 for the treatment of a bacterial infection caused by *Staph aureus.* wherein an amount sufficient to be effective against said *Staph. aureus* infection is administered.

113. A method according to claim 40 for the treatment of a bacterial infection caused by *Klebsiella aerogenes* wherein an amount sufficient to be effective against said *Klebsiella aerogenes* infection is administered.

114. A method according to claim 68 wherein the moiety of the formula (d) is —$CH(CH_3)$—$CO_2A_5$ wherein $A_5$ is methyl, ethyl, propyl, butyl, phenyl or benzyl.

* * * * *

UNITED STATES PATENT AND TRADEMARK OFFICE
CERTIFICATE OF CORRECTION

PATENT NO. : 4,343,807

DATED : August 10, 1982

INVENTOR(S) : Irene Stirling, et al

It is certified that error appears in the above-identified patent and that said Letters Patent are hereby corrected as shown below:

IN THE CLAIMS:

Claim 1, penultimate and last lines, delete "; with the proviso that if m and n are both 1, then A is $-CH_2-$ and $R^2$ is not oxo".

Claim 3, penultimate line, after "wherein" insert --A is oxygen or sulphur and--.

Cancel claim 4.

Renumber claims 5-20 as claims 4-19.

Claim 19 (now claim 18), line 2, delete "or sulphur".

Cancel claim 21.

Renumber claims 22-27 as claims 20-25.

Cancel claims 28-34.

Renumber claims 35-37 as claims 26-28.

Cancel claim 38.

Renumber claims 39-44 as claims 29-34.

Claim 39 (now claim 29), fourth to last line to penultimate line, delete ", with the proviso that if m and n are both 1 then A is $-CH_2-$ and $R^2$ is not oxo".

Claim 40 (now claim 30), fourth to last line and third to last line, delete "with the proviso that if m and n are both 1 then A is $-CH_2-$ and $R^2$ is not oxo".

UNITED STATES PATENT AND TRADEMARK OFFICE
CERTIFICATE OF CORRECTION

PATENT NO. : 4,343,807
DATED : August 10, 1982
INVENTOR(S) : Irene Stirling, et al It is certified that error appears in the above-identified patent and that said Letters Patent are hereby corrected as shown below:

Cancel claim 45.
Renumber claims 46-53 as claims 35-42.
Cancel claim 54.
Renumber claims 55-60 as claims 43-48.
Cancel claims 61-67.
Renumber claims 68-85 as claims 49-66.
Cancel claim 86.
Renumber claims 87-95 as claims 67-74.
Cancel claim 95.
Renumber claims 96-101 as claims 75-80.
Cancel claims 102-108.
Renumber claims 109-114 as claims 81-86.
On the title page after abstract, "114 Claims" should read -- 86 Claims --.

Signed and Sealed this

Fourteenth Day of February 1984

[SEAL]

Attest:

GERALD J. MOSSINGHOFF

Attesting Officer

Commissioner of Patents and Trademarks